(12) United States Patent
Hwang et al.

(10) Patent No.: US 11,298,067 B2
(45) Date of Patent: Apr. 12, 2022

(54) METHOD FOR CLASSIFYING TYPE OF HEARTBEAT AND APPARATUS USING THE SAME

(71) Applicant: University of Seoul Industry Cooperation Foundation, Seoul (KR)

(72) Inventors: Heasoo Hwang, Seoul (KR); Sellami Ali, Seoul (KR)

(73) Assignee: University of Seoul Industry Cooperation Foundation, Seoul (KR)

(*) Notice: Subject to any disclaimer, the term of this patent is extended or adjusted under 35 U.S.C. 154(b) by 190 days.

(21) Appl. No.: 16/439,949

(22) Filed: Jun. 13, 2019

(65) Prior Publication Data
US 2020/0289010 A1 Sep. 17, 2020

(30) Foreign Application Priority Data
Mar. 14, 2019 (KR) .................. 10-2019-0029331

(51) Int. Cl.
| | |
|---|---|
| A61B 5/352 | (2021.01) |
| G06N 3/08 | (2006.01) |
| A61B 5/364 | (2021.01) |
| A61B 5/361 | (2021.01) |
| A61B 5/366 | (2021.01) |
| A61B 5/00 | (2006.01) |
| A61B 5/024 | (2006.01) |
| A61B 5/316 | (2021.01) |
| A61B 5/363 | (2021.01) |

(52) U.S. Cl.
CPC .............. *A61B 5/352* (2021.01); *A61B 5/364* (2021.01); *A61B 5/7267* (2013.01); *G06N 3/08* (2013.01); *A61B 5/02438* (2013.01); *A61B 5/316* (2021.01); *A61B 5/361* (2021.01); *A61B 5/363* (2021.01); *A61B 5/366* (2021.01); *A61B 5/7203* (2013.01)

(58) Field of Classification Search
CPC ....... A61B 5/352; A61B 5/364; A61B 5/7267; A61B 5/361; A61B 5/363; A61B 5/366; A61B 5/316; A61B 5/02438; A61B 5/7203; G06N 3/08
See application file for complete search history.

(56) References Cited

FOREIGN PATENT DOCUMENTS

KR 10-1912090 B1 10/2018

OTHER PUBLICATIONS

He K, et al. Deep residual learning for image recognition. IEEE Conference on Computer Vision and Pattern Recognition. 2016 (Year: 2016).*

(Continued)

*Primary Examiner* — Mallika D Fairchild
*Assistant Examiner* — Shreya Anjaria
(74) *Attorney, Agent, or Firm* — Hamre, Schumann, Mueller & Larson, P.C.

(57) ABSTRACT

A method for classifying types of heartbeats includes obtaining a dataset including multiple heartbeat waveform data, generating, from the dataset, input data regarding a heartbeat waveform for training and generating a learning model to which the generated input data is input and from which a heartbeat type of the heartbeat waveform for training is output, training the learning model by determining a loss weight of each batch sampled from the dataset and determining a loss function based on the loss weight of each batch, and inputting a heartbeat waveform for test to the learning model and classifying a heartbeat type of the heartbeat waveform for test.

11 Claims, 5 Drawing Sheets

(56) References Cited

OTHER PUBLICATIONS

Ioffe S, et al. Batch normalization: accelerating deep network training by reducing internal covariate shift. Proceedings of the 32nd International Conference on Machine Learning. 2015 (Year: 2015).*
Sellami, Ali and Hwang, Heasoo. A robust deep convolutional neural network with batch-weighted loss for heartbeat classification. Expert Systems With Applications, vol. 122, pp. 75-84. Available online Dec. 2018 (Year: 2018).*
Convolutional Neural Network. [online]. MathWorks [retrieved on Feb. 11, 2021]. Retrieved from the Internet: <URL: https://www.mathworks.com/discovery/convolutional-neural-network-matlab.html#cnns-with-matlab>.*
Acharya et al., 2017, "A deep convolutional neural network model to classify heartbeats", Computers in Biology and Medicine, 8 pages provided.
DeChazal, et al., "Automatic Classification of Heartbeats Using ECG Morphology and Heartbeat Interval Features", IEEE Transactions on Biomedical Engineering, vol. 51, No. 7, Jul. 2004, 11 pages provided.
Li, T., & Zhou, 2016, "ECG classification using wavelet packet entropy and random forests", www.mdpi.com/journal/entropy, 16 pages provided.
Huang et al., 2014, "A new hierarchical method for inter-patient heartbeat classification using random projections and RR intervals", BioMedical Engineering OnLine, 26 pages provided.

\* cited by examiner

METHOD FOR CLASSIFYING TYPE OF HEARTBEAT AND APPARATUS USING THE SAME

TECHNICAL FIELD

The present disclosure relates to a method for classifying types of heartbeats and an apparatus using the same.

BACKGROUND

The early detection of abnormal heart rhythm has become crucial due to the spike in the rate of deaths caused by cardiovascular diseases. Particularly, interpreting electrocardiography (ECG) signal is important to detect abnormal heart rhythms.

Recently, various types of single-lead portable ECG devices such as chest patches and wristbands have become more widely available. As the amount of ECG data that is continuously collected using these devices grows rapidly, the interest in the effective detection of important arrhythmias such as atrial fibrillation, one of the leading causes of stroke, is growing as well.

However, the conventional methods for classifying types of heartbeats heavily rely on data preprocessing such as noise removal and feature extraction, which is computationally expensive, and thus limit the use of low-cost portable ECG devices such as single-lead portable ECG devices.

Meanwhile, the Association for the Advancement of Medical Instrumentation (AAMI) classifies heartbeat types into five classes, i.e., N, S, V, F, and Q, as shown in Table 1.

TABLE 1

| AAMI classes | N (Non-ectopic) | S (Supraventricular ectopic beat) | V (Ventricular ectopic beat) | F (Fusion beat) | Q (Unknown beat) |
|---|---|---|---|---|---|
| Heartbeat types | Normal beat Left bundle branch block beat Right bundle branch block beat Atrial escape beat Nodal (junctional) escape beat | Atrial premature beat Aberrated atrial premature beat Nodal (junctional) premature beat Supraventricular premature beat | Premature ventricular contraction Ventricular escape beat | Fusion of ventricular and normal beat | Paced beat Fusion of paced and normal beat Unclassifi-able beat |

FIG. 1 shows an ECG waveform of a heartbeat. The ECG waveform in FIG. 1 shows a change in intensity of electrical signal when the heart beats once.

The ECG waveform of a heartbeat includes components such as P wave, QRS wave, T wave, U wave, PR interval, QT interval, ST segment, and the like. The P wave is a signal related to the depolarization of the atria caused by the spread of impulse from the sinoatrial node throughout the atria.

The QRS wave includes three Q, R and S waves and is a signal related to the depolarization of the ventricles. The ventricles cause depolarization very fast like the atria because the speed is much higher in the His-Purkinje system than in the atrial conduction system.

The T wave is a signal related to the repolarization of the ventricles and is not uniform in height and width. The U wave is a slow wave generated at the end of repolarization of the ventricles and begins gradually or suddenly from the baseline or begins from a slope in the latter half of the T wave.

The PR interval represents the period from the beginning of atrial depolarization until the beginning of ventricular depolarization. The QT interval represents the period from the first ventricular depolarization to the last ventricular repolarization. The ST segment represents early repolarization of the left and right ventricles, i.e., depolarization of entire ventricular muscle.

Since the ST segment refers to the depolarization of entire ventricular muscle, a voltage which is not at the baseline means that all ventricular muscle cells are not depolarized simultaneously and also means a pathological symptom such as myocardial infarction.

A condition in which the heartbeat is too slow, too fast, or irregular, i.e., abnormal heartbeat, is called arrhythmia.

These five classes of heartbeats have a problem of imbalance between classes, and, thus, the performance, e.g., accuracy in classifying heartbeats is low.

That is, as can be seen from Table 2, the class N occupies 89.05% of the full dataset, while the other four classes S, V, F, and Q account for 2.74%, 6.93%, 0.79%, and 0.48% respectively. The dataset shown in Table 2 is just an example and other datasets can be used.

TABLE 2

MIT-BIH arrhythmia database

| Heartbeat Class | | N | S | V | F | Q | Total |
|---|---|---|---|---|---|---|---|
| DS1 + DS2 | Number of beats | 90070 | 2781 | 7007 | 802 | 15 | 100675 |
| | % | 89.47 | 2.76 | 6.96 | 0.80 | 0.01 | 100.00 |
| DS1 | Number of beats | 45839 | 944 | 3788 | 414 | 8 | 50993 |
| | % | 89.89 | 1.85 | 7.43 | 0.81 | 0.02 | 100.00 |
| DS2 | Number of beats | 44231 | 1837 | 3219 | 388 | 7 | 49682 |
| | % | 89.03 | 3.70 | 6.48 | 0.78 | 0.01 | 100.00 |

To overcome this problem, conventional methods for classifying types of heartbeats have tried to integrate synthetic data and increase the size of input data. However, since synthetic data is generated directly from the given original data, the probability of generating biased results may be high and training time may be increased.

Prior Art Document: Korean Patent No. 10-1912090

SUMMARY

In view of the foregoing, the present disclosure provides a method for classifying types of heartbeats and an apparatus using the same to minimize an imbalance in a dataset between classes by determining a loss function based on loss weights of each batch and training a learning model.

However, problems to be solved by the present disclosure are not limited to the above-described problems. There may be other problems to be solved by the present disclosure.

According to an aspect of the present disclosure, a method for classifying types of heartbeats includes obtaining a dataset including multiple heartbeat waveform data, generating, from the dataset, input data regarding a heartbeat waveform for training and generating a learning model to which the generated input data is input and from which a heartbeat type of the heartbeat waveform for training is output, training the learning model by determining a loss weight of each batch sampled from the dataset and determining a loss function based on the loss weight of each batch, and inputting a heartbeat waveform for test to the learning model and classifying a heartbeat type of the heartbeat waveform for test.

According to another aspect of the present disclosure, an apparatus for classifying types of heartbeats includes a storage unit configured to store a dataset including multiple heartbeat waveform data, a learning model generation unit configured to generate, from the dataset, input data regarding a heartbeat waveform for training and generate a learning model to which the generated input data is input and from which a heartbeat type of the heartbeat waveform for training is output, a training unit configured to train the learning model by determining a loss weight of each batch sampled from the dataset and determining a loss function based on the loss weight of each batch, and a classification unit configured to input a heartbeat waveform for test to the learning model and classify a heartbeat type of the heartbeat waveform for test.

The above-described aspects are provided by way of illustration only and should not be construed as limiting the present disclosure. Besides the above-described embodiments, there may be additional embodiments described in the accompanying drawings and the detailed description.

According to any one of the aspects of the present disclosure, it is possible to minimize an imbalance between classes in a dataset by determining a loss function based on a loss weight of each batch and training a learning model.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

DETAILED DESCRIPTION

Figure 1:
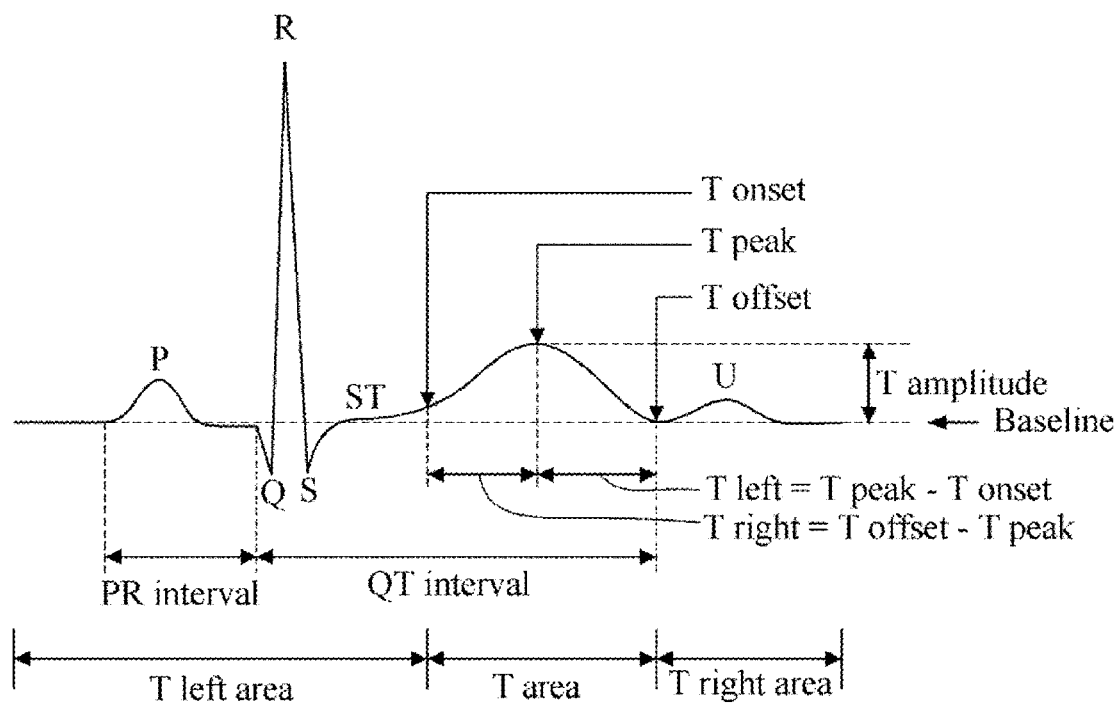
FIG. 1 shows an ECG waveform of a heartbeat.

Hereafter, example embodiments will be described in detail with reference to the accompanying drawings so that the present disclosure may be readily implemented by those skilled in the art. However, it is to be noted that the present disclosure is not limited to the example embodiments but can be embodied in various other ways. In the drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element. Further, it is to be understood that the term "comprises or includes" and/or "comprising or including" used in the document means that one or more other components, steps, operation and/or existence or addition of elements are not excluded in addition to the described components, steps, operation and/or elements unless context dictates otherwise and is not intended to preclude the possibility that one or more other features, numbers, steps, operations, components, parts, or combinations thereof may exist or may be added.

Throughout this document, the term "unit" includes a unit implemented by hardware and/or a unit implemented by software. As examples only, one unit may be implemented by two or more pieces of hardware or two or more units may be implemented by one piece of hardware.

In the present specification, some of operations or functions described as being performed by a device may be performed by a server connected to the device. Likewise, some of operations or functions described as being performed by a server may be performed by a device connected to the server.

An example embodiment of the present disclosure will be described in detail with reference to the accompanying drawings.

Figure 2:
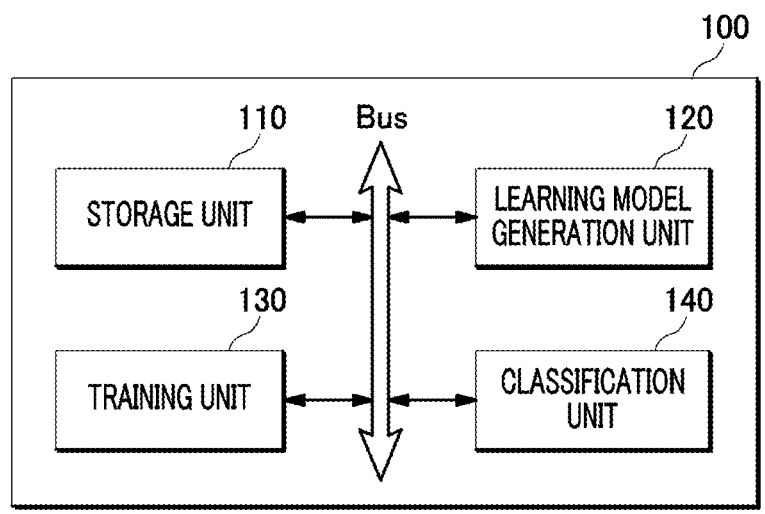
FIG. 2 is a block diagram illustrating a heartbeat type classifying apparatus in accordance with various embodiments described herein.

FIG. 2 is a block diagram illustrating a heartbeat type classifying apparatus in accordance with various embodiments described herein. Referring to FIG. 2, a heartbeat type classifying apparatus 100 may include a storage unit 110, a learning model generation unit 120, a training unit 130, and a classification unit 140.

Herein, heartbeat types may refer to five classes, i.e., N, S, V, F, and Q, defined by the AAMI.

The storage unit 110 may store a dataset including multiple heartbeat waveform data. For example, the dataset may include ECG data (ECG records) which were digitized at 360 samples.

The dataset may include a first dataset DS1 (see Table 2) to be used for training and a second dataset DS2 (see Table 2) to be used for test.

The learning model generation unit 120 may generate, from the dataset, input data regarding a heartbeat waveform for training and generate a learning model to which the generated input data is input and from which a heartbeat type of the heartbeat waveform for training is output.

For example, the learning model generation unit 120 may browse heartbeat waveforms in the dataset to capture the most important waves that define a heartbeat and then set the extraction window size.

For example, the learning model generation unit 120 may extract a heartbeat waveform for training by extracting, from the ECG data, 70 samples before an R-peak and 100 samples after the R-peak and using an extraction window of 170 samples around each R-peak location.

That is, the heartbeat waveform for training may include a heartbeat waveform of a predetermined number of samples around the R-peak which is extracted from the ECG data. Herein, a fast R-peak detection algorithm may be used to detect R-peak locations.

Figure 3:
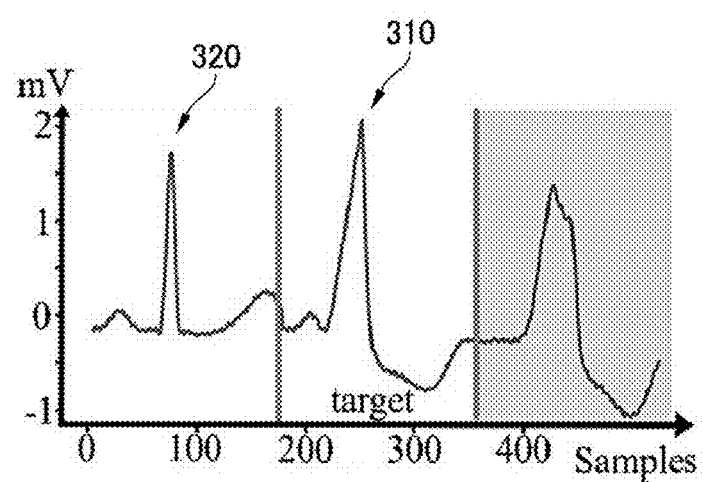
FIG. 3 is a depiction to explain input data for a learning model in accordance with various embodiments described herein.

Referring to FIG. 3 briefly, the input data may include a target heartbeat waveform 310, a heartbeat type (i.e., one of N, S, V, F, and Q) of the target heartbeat waveform 310, and a neighboring heartbeat waveform 320 adjacent to the target heartbeat waveform 310. Herein, the neighboring heartbeat waveform 320 may refer to a heartbeat waveform right before the target heartbeat waveform 310.

The type of a heartbeat is determined not only by the morphology of a heartbeat but also by the heartbeat rhythm composed of its neighboring heartbeats. Therefore, by including the neighboring heartbeat waveforms in the input data, the accuracy in classifying types of heartbeats can be improved.

Referring to FIG. 2 again, the conventional methods for classifying types of heartbeats have tried to integrate synthetic data and increase the size of input data as described above, whereas the method of the present disclosure uses the original data without adding any extra data and thus reduces training time and does not generate biased results.

In the present disclosure, a batch-weighted loss function is used to achieve high classification performance with the original data only.

To be specific, the training unit 130 may train the learning model by determining a loss weight of each batch sampled from the dataset and determining a loss function based on the loss weight of each batch.

Herein, the loss weight of each batch may be calculated based on the following Equation 1.

$$cw_{i,class_k} = 1 - \frac{\sum_{j=1}^{M} 1_{y_{i,j}=class_k}}{M} + \varepsilon \quad \text{[Equation 1]}$$

where M is a batch size, E is a predetermined constant, $cw_{i,class_k}$ is a loss weight of a kth class in an ith batch, and $y_{i,j}$ is a label (i.e., N, S, V, F, or Q) of a jth class in the ith batch.

For example, E may be 0.02 in order for the loss weight not to be 0 when $y_{i,j}$ contains only one class.

The loss function $L_i$ is a cross entropy loss function and may be calculated based on the following Equation 2:

$$L_i = -\sum_{j=1}^{M} cw_{i,y_{i,j}} y_{i,j} \log \hat{y}_{i,j} + \lambda \|W\|_2^2 \quad \text{[Equation 2]}$$

where $\hat{y}_{i,j}$ is a predicted probability of a jth training instance in the ith batch, W is weight matrices of all the layers, and λ is L$_2$ regularization parameter. For example, A may be set to 0.01.

According to Equations 1 and 2, the loss weight and the loss function dynamically change as the distribution of classes in each batch changes.

In general, if an ECG waveform from a single lead is used without data preprocessing, the classification accuracy is greatly decreased. Actually, in many studies, careful preprocessing and data from multiple leads are used to improve the classification accuracy.

However, such careful preprocessing requires a lot of time and data from multiple leads cannot be collected by a typical watch- or patch-type sensor.

To overcome this problem, the loss function according to Equation 2 is used in the present disclosure. Therefore, even though an ECG waveform from a single lead is used without any data preprocessing such as noise removal and feature extraction, the heartbeat type classifying apparatus 100 can have high classification performance.

Further, since data preprocessing is not performed, real-time heartbeat type classification can be performed using a single-lead portable ECG device.

Figure 4:
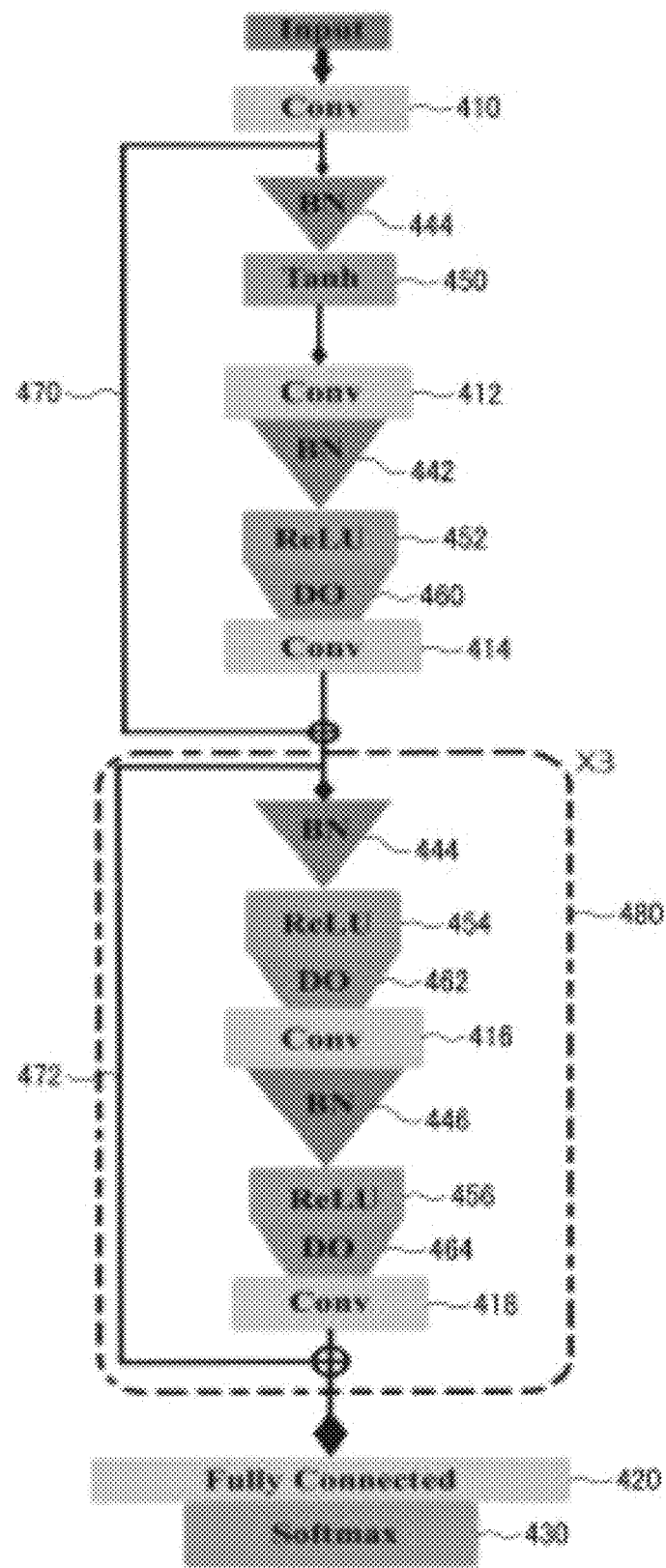
FIG. 4 is an example illustration of a learning model in accordance with various embodiments described herein.

FIG. 4 is an example illustration of a learning model in accordance with various embodiments described herein.

Referring to FIG. 4, the learning model may be based on a Convolution Neural Network (CNN). For example, the learning model may include multiple convolutional layers 410, 412, 414, 416, and 418, at least one fully connected layer 420, and a softmax function layer 430.

A set of layers denoted by reference numeral 480 in FIG. 4 is repeated three times, but the illustration thereof is omitted in the drawing.

Herein, the number of nodes in an input layer of the learning model may correspond to the number of samples in each input data (e.g., 340 samples (170 samples for target beat and 170 samples for previous beat)).

For example, the learning model may include nine convolutional layers. That is, the learning model may include three convolutional layers 410, 412, and 414 and six convolutional layers 416 and 418 included in the set of layers denoted by reference numeral 480.

Herein, each of the convolutional layers 410, 412, 414, 416, and 418 may has 64 k kernels with a length of 16, where k starts from 1 and increases by 1 per two convolutional layers.

Since the convolutional layers 410, 412, 414, 416, and 418 are configured as described above, details of the input (heartbeat waveform) can be considered well, and, thus, the classification accuracy can be improved.

That is, in the present disclosure, an end-to-end deep convolutional neural network is constructed by batch normalization of the convolutional layers 410, 412, 414, 416, and 418, proper use of dropout, and proper use of activation functions such as Tanh (hyperbolic tangent), ReLU (Rectified Linear Unit), and the like, and, thus, high classification performance can be achieved.

The learning model may further include batch normalization layers 440, 442, 444, and 446 connected to the multiple convolutional layers 410, 412, 414, 416, and 418 respectively.

The learning model of the present disclosure uses the nine convolutional layers and thus needs a long training time to train the end-to-end deep convolutional neural network. Therefore, the batch normalization layers 440, 442, 444, and 446 may be placed with the respective convolutional layers 410, 412, 414, 416, and 418 to reduce the training time.

Herein, the batch normalization layers 440, 442, 444, and 446 may perform a batch normalization based on the following Equation 3:

$$BN_{C_i} = \frac{x_{C_i} - \mu_\beta(x_{C_i})}{\sqrt{\sigma_\beta^2(x_{C_i})}} \quad \text{[Equation 3]}$$

where $X_{C_i}$ is an output of an ith convolutional layer, and $\mu_\beta(X_{C_i})$ is the mean and $\sigma_\beta(X_{C_i})$ is the variance of output values after values in a batch pass through the ith convolutional layer, and $BN_{C_i}$ is an output after applying the batch normalization.

The learning model may further include activation functions 450, 452, 454, and 456. A Tanh function or ReLu function may be used as the activation functions.

The activation functions 450, 452, 454, and 456 may be connected to the batch normalization layers 440, 442, 444, and 446.

To be specific, the ReLu function may be used after the first convolutional layer 410 and the ReLU function may be used after each of the other convolutional layers 412, 414, and 416.

If the ReLU function is used after the first convolutional layer 410, it converts all the negative values into 0. Therefore, it is likely that important heartbeat features from the first convolutional layer 410 are lost.

Accordingly, in the present disclosure, the Tanh function is used after the first convolutional layer 410, and, thus, a large amount of information can be well preserved in the kernels and fed to the following convolutional layers 412, 414, and 416 to preserve important heartbeat features from the first convolutional layer 410.

Meanwhile, a deep convolutional neural network may overfit the training data, which may seriously degrade the classification performance. That is, when the layers are excessively deep, the deep convolutional neural network may be not suitable for training but may be degraded in performance.

In the present disclosure, the learning model may further include multiple dropout layers 460, 462, and 464 with 75% dropout to suppress overfitting.

The dropout layers 460, 462, and 464 may be located before layers that are prone to overfitting, i.e., the third through ninth convolutional layers 414, 416, and 418.

The learning model may further include multiple residual connections to suppress the degradation of training performance.

For example, the learning model may include multiple skip connections 470 and 472. The skip connection 470 may skip the second and third convolutional layers 412 and 414. Further, the skip connection 472 may skip the fourth and fifth convolutional layers 416 and 418 (or the sixth and seventh convolutional layers or the eighth and ninth convolutional layers).

The classification unit 140 may input a heartbeat waveform for test to the learning model and classify a heartbeat type of the heartbeat waveform for test.

Herein, the heartbeat waveform for test may be an ECG waveform input from a single lead. Also, multiple leads can be used with changing the input size.

Figure 5:
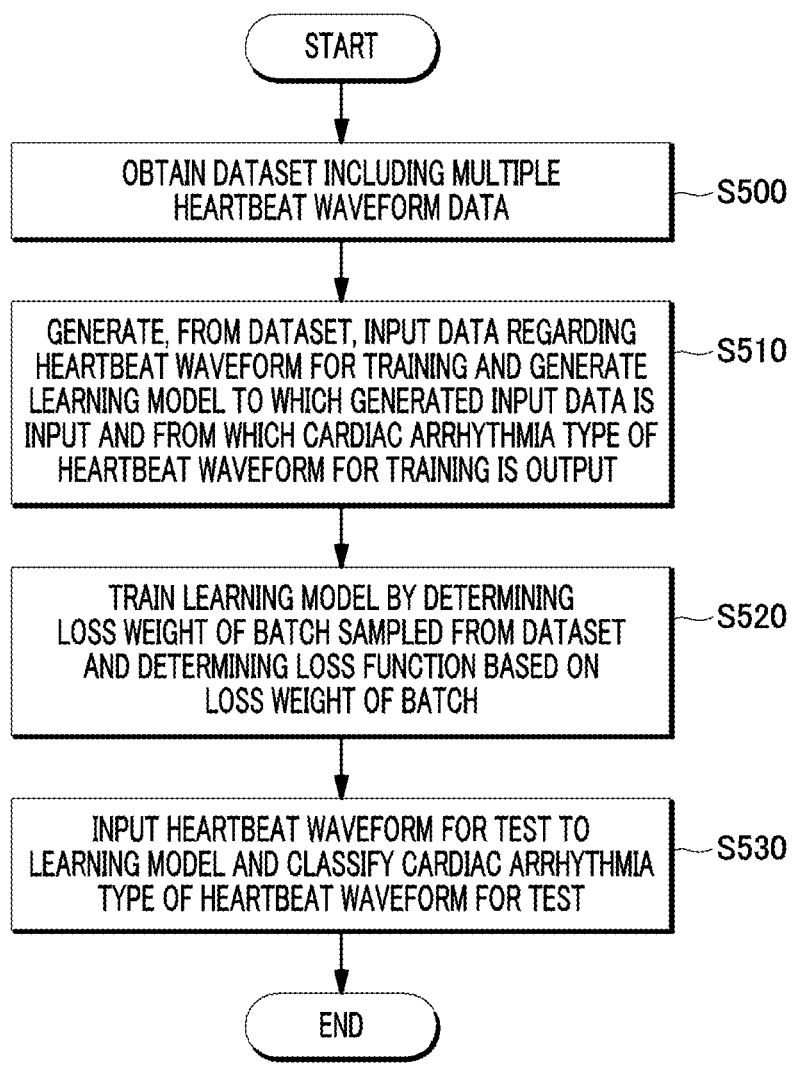
FIG. 5 is a flowchart illustrating a method for classifying types of heartbeats in accordance with various embodiments described herein.

FIG. 5 is a flowchart illustrating a method for classifying types of heartbeats in accordance with various embodiments described herein.

The method for classifying types of heartbeats according to the embodiment illustrated in FIG. 5 includes the processes time-sequentially performed by the heartbeat type classifying apparatus illustrated in FIG. 2. Therefore, descriptions of the processes performed by the heartbeat type classifying apparatus may be applied to the method for classifying types of heartbeats according to the embodiment illustrated in FIG. 5, even though they are omitted hereinafter.

Referring to FIG. 5, in process S500, a dataset including multiple heartbeat waveform data is obtained.

In process 520, input data regarding a heartbeat waveform for training is generated from the dataset and a learning model to which the generated input data is input and from which a heartbeat type of the heartbeat waveform for training is output is generated.

In process 520, the learning model is trained by determining a loss weight of each batch sampled from the dataset and determining a loss function based on the loss weight of each batch.

In process S530, a heartbeat waveform for test is input to the learning model to classify a heartbeat type of the heartbeat waveform for test.

The method for classifying types of heartbeats described above with reference to FIG. 5 can be embodied in a computer program stored in a medium or in a storage medium including instruction codes executable by a computer such as a program module executed by the computer. A computer-readable medium can be any usable medium which can be accessed by the computer and includes all volatile/non-volatile and removable/non-removable media. Further, the computer-readable medium may include all computer storage media. The computer storage media include all volatile/non-volatile and removable/non-removable media embodied by a certain method or technology for storing information such as computer-readable instruction code, a data structure, a program module or other data.

In the following, the performance metrics, accuracy, positive productivity, sensitivity and specificity, will be compared with the conventional methods for classifying types of heartbeats (herein, the performance metrics were calculated according to the guidelines provided by the AAMI).

For comparison with the conventional methods for classifying types of heartbeats, the aggregate performance measures (the gross statistics or the averages) that assign equal weight to each heartbeat just as many prior documents were used.

For performance comparison under intra-patient paradigm, 10-fold cross-validation was performed as in Reference 1 (Acharya et al., 2017, A deep convolutional neural network model to classify heartbeats) to obtain a confusion matrix.

Table 3 shows the data comparing the present disclosure with Reference 1.

TABLE 3

| | | Accuracy | Positive productivity | Sensitivity | Specificity |
|---|---|---|---|---|---|
| Class | N | 99.56% | 99.65% | 99.87% | 96.99% |
| | S | 99.68% | 97.27% | 90.83% | 99.93% |
| | V | 99.86% | 98.93% | 99.06% | 99.92% |
| | F | 99.86% | 92.69% | 90.15% | 99.94% |
| | Q | 100.00% | 100.00% | 93.33% | 100.00% |
| Present disclosure | | 99.48% | 98.83% | 96.97% | 99.87% |
| Reference 1 (Imbalanced) | | 89.03% | 62.29% | 95.74% | 88.39% |
| Reference 1 (Balanced) | | 94.03% | 97.81% | 96.64% | 91.54% |

Reference 1 constructed a deep convolutional neural network of nine layers with input data obtained after noise removal. As shown in Table 3, Reference 1 also measured the heartbeat classification performance with both imbalanced and balanced input data. Further, Reference 1 obtained balanced input data by adding synthetic data generated by varying the standard deviation and mean of Z-score from the original imbalanced ECG data.

Table 3 confirmed that the present disclosure significantly outperforms the method of Reference 1 with imbalanced input data. Table 3 also confirmed that the present disclosure shows a superior performance in all aspects to Reference 1 with balanced input data.

Further, Reference 1 may add synthetic data directly generated from the original input data to produce biased results. At the same time, Reference 1 increases the training time significantly when the degree of imbalance in the original input data is high.

Table 4 shows the data comparing the present disclosure with Reference 2 (deChazal, et al., 2004, Automatic Classification of Heartbeats Using ECG Morphology and Heartbeat Interval Features), Reference 3 (Li, T., & Zhou, 2016, ECG classification using wavelet packet entropy and random forests), and Reference 4 (Huang et al., 2014, A new hierarchical method for inter-patient heartbeat classification using random projections and RR intervals) under inter-patient paradigm.

TABLE 4

| | Accuracy | Positive productivity | Sensitivity | Specificity |
|---|---|---|---|---|
| Present disclosure | 88.34% | 48.25% | 90.90% | 88.51% |
| Referecnce 2 | 85.88% | 42.21% | 92.85% | 86.86% |
| Referecnce 3 | 94.61% | 38.03% | 51.77% | — |
| Referecnce 4 | 94.55% | 66.88% | 96.91% | 94.74% |
| Present disclosure (3-class) | 95.08% | 68.65% | 96.26% | 95.00% |

It could be seen that the present disclosure is superior in classification performance, i.e., accuracy (88.34%→85.88%), positive productivity (48.25%→42.21%), and specificity (88.51%→86.86%), to Reference 2, but Reference 2 is superior in sensitivity (90.90%→92.85%).

It could be seen that the positive productivity and sensitivity of Reference 3 are only 38.03% and 51.77%, whereas the positive productivity and sensitivity of the present disclosure are 55.59% and 69.04% respectively.

Reference 4 showed the highest performance results. However, Reference 4 constructed a heartbeat classifier for classifying three classes, whereas the present disclosure and the other References targeted on classifying all the five classes suggested by the AAMI.

It could be seen that if the present disclosure considers only three classes like Reference 4, the present disclosure outperforms Reference 4 except for sensitivity (96.26%→96.91%).

The above description of the present disclosure is provided for the purpose of illustration, and it would be understood by a person with ordinary skill in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A method for detecting abnormal heart rhythm from classified types of heartbeats, comprising:

obtaining a dataset including multiple heartbeat waveform data;

generating, from the dataset, input data including characteristics of a heartbeat waveform for training and generating a learning model to which the generated input data is input and from which a heartbeat type of the heartbeat waveform for training is output;

minimizing an imbalance in the dataset between the classified types of heartbeats by training the learning model by determining a loss weight of each batch sampled from the dataset and determining a loss function based on the loss weight of each batch;

inputting a heartbeat waveform for test to the learning model and classifying a heartbeat type of the heartbeat waveform for test, wherein the loss weight of each batch is calculated based on the following equation:

$$cw_{i, class_k} = 1 - \frac{\sum_{j=1}^{M} 1_{y_{i,j} = class_k}}{M} + \varepsilon$$

wherein M is a batch size, $\varepsilon$ is a predetermined constant, $cw_{i, class_k}$ is a loss weight of a kth class in an $i^{th}$ batch; and using at least a single lead that produces an electrocardiogram waveform as an input to the trained learning model which outputs the heartbeat type to detect an abnormal heart rhythm, wherein the electrocardiogram waveform is used without any data preprocessing.

2. The method for classifying types of heartbeats of claim 1, wherein the input data includes a target heartbeat waveform, a heartbeat type of the target heartbeat waveform, and a neighboring heartbeat waveform adjacent to the target heartbeat waveform.

3. The method for classifying types of heartbeats of claim 1, wherein the heartbeat waveform for training includes a heartbeat waveform of a predetermined number of samples around an R-peak which is extracted from electrocardiography (ECG) data.

4. The method for classifying types of heartbeats of claim 1, wherein the loss function is calculated based on the following equation:

$$L_i = -\sum_{j=1}^{M} cw_{i, y_{i,j}} y_{i,j} \log \hat{y}_{i,j} + \lambda \|W\|_2^2$$

wherein $\hat{y}_{i,j}$ is a predicted probability of a jth training instance in the $i^{th}$ batch, W is weight matrices of all the layers, $\lambda$ is $L_2$ regularization parameter and $L_i$ is the loss function.

5. The method for classifying types of heartbeats of claim 1, wherein the learning model includes multiple convolutional layers, at least one fully connected layer, and a softmax function layer.

6. The method for classifying types of heartbeats of claim 5, wherein the learning model further includes batch normalization layers, each normalization layer connected to a respective one of the multiple convolutional layers.

7. The method for classifying types of heartbeats of claim 6, wherein the batch normalization layers perform a batch normalization based on the following equation:

$$BN_{C_i} = \frac{x_{C_i} - \mu_\beta(x_{C_i})}{\sqrt{\sigma_\beta^2(x_{C_i})}}$$

wherein $X_{C_i}$ is an output of an ith convolutional layer, and $\mu_\beta(X_{C_i})$ is the mean and $\sigma_\beta(X_{C_i})$ is the variance of output values after values in a batch pass through the ith convolutional layer, and $BN_{C_i}$ is an output after applying the batch normalization.

8. The method for classifying types of heartbeats of claim 5, wherein the learning model further includes at least one skip connection.

9. An apparatus for detecting abnormal heart rhythm from classified types of heartbeats, comprising:
- a single lead configured to produce an electrocardiogram waveform, wherein the electrocardiogram waveform is used without any data preprocessing;
- a storage unit configured to store a dataset including multiple heartbeat waveform data;
- a learning model generation unit configured to generate, from the dataset, input data regarding a heartbeat waveform for training and generate a learning model to which the generated input data is input and from which a heartbeat type of the heartbeat waveform for training is output;
- a training unit configured to train the learning model by determining a loss weight of each batch sampled from the dataset and determining a loss function based on the loss weight of each batch; and
- a classification unit configured to input a heartbeat waveform for test to the learning model and classify a heartbeat type of the heartbeat waveform for test, wherein the loss weight of each batch is calculated based on the following equation:

$$cw_{i,class_k} = 1 - \frac{\sum_{j=1}^{M} 1_{y_{i,j}=class_k}}{M} + \varepsilon$$

wherein M is a batch size, E is a predetermined constant, $cw_{i,class_k}$ is a loss weight of a $k^{th}$ class in an $i^{th}$ batch, wherein the classification unit is also configured to use the electrocardiogram waveform produced by the single lead to detect an abnormal heart rhythm based on the heartbeat type output from the trained learning model.

10. The apparatus for classifying types of heartbeats of claim 9, wherein the input data includes a target heartbeat waveform, a heartbeat type of the target heartbeat waveform, and a neighboring heartbeat waveform adjacent to the target heartbeat waveform.

11. The apparatus for classifying types of heartbeats of claim 9, wherein the loss function is calculated based on the following equation:

$$L_i = -\sum_{j=1}^{M} cw_{i,y_{i,j}} y_{i,j} \log \hat{y}_{i,j} + \lambda \|W\|_2^2$$

where $\hat{y}_{i,j}$ is a predicted probability of a jth training instance in the ith batch, W is weight matrices of all the layers, $\lambda$ is $L_2$ regularization parameter and $L_i$ is the loss function.

* * * * *